(12) United States Patent
Hoffer et al.

(10) Patent No.: US 8,163,963 B2
(45) Date of Patent: Apr. 24, 2012

(54) PROCESS FOR CONTINUOUS HYDROGENATION OR HYDROGENATING AMINATION

(75) Inventors: Bram Willem Hoffer, Heidelberg (DE); Hartwig Voβ, Frankenthal (DE); Ekkehard Schwab, Neustadt (DE); Udo Rheude, Otterstadt (DE); Gerd Kaibel, Lampertheim (DE); Mathias Haake, Hong Kong (HK); Jan Eberhardt, Mannheim (DE); Michael Karcher, Schwetzingen (DE)

(73) Assignee: BASF SE, Ludwigschafen (DE)

( * ) Notice: Subject to any disclaimer, the term of this patent is extended or adjusted under 35 U.S.C. 154(b) by 487 days.

(21) Appl. No.: 12/090,377

(22) PCT Filed: Oct. 16, 2006

(86) PCT No.: PCT/EP2006/067470
§ 371 (c)(1),
(2), (4) Date: Jul. 29, 2008

(87) PCT Pub. No.: WO2007/045641
PCT Pub. Date: Apr. 26, 2007

(65) Prior Publication Data
US 2010/0081804 A1    Apr. 1, 2010

(30) Foreign Application Priority Data
Oct. 17, 2005  (DE) .................. 10 2005 049 568

(51) Int. Cl.
*C07C 45/00*    (2006.01)

(52) U.S. Cl. ..................................... 568/434
(58) Field of Classification Search .................. 568/434
See application file for complete search history.

(56) References Cited

U.S. PATENT DOCUMENTS

| 6,150,564 A | 11/2000 | Brocker et al. |
| 6,723,883 B1 * | 4/2004 | Therre et al. .................. 568/433 |
| 6,930,213 B1 | 8/2005 | Pompetzki et al. |
| 7,667,058 B2 * | 2/2010 | Anderson et al. ............. 554/141 |

FOREIGN PATENT DOCUMENTS

| CA | 1122981 A1 | 5/1982 |
| CN | 1234385 A | 11/1999 |
| CN | 1281842 A | 1/2001 |
| DE | 196 25 189 C1 | 10/1997 |
| EP | 0 947 493 A1 | 10/1999 |
| JP | 55015463 A | 2/1980 |
| JP | 11349517 A | 12/1999 |

OTHER PUBLICATIONS

Ullmanns Enzyklopaedie der Technischen Chemie, 4th Edition, VCH, vol. 13, p. 138, 1997.

* cited by examiner

*Primary Examiner* — Rebecca Anderson
*Assistant Examiner* — Samantha Shterengarts
(74) *Attorney, Agent, or Firm* — Connolly Bove Lodge & Hutz LLP

(57) ABSTRACT

A process is described for continuously hydrogenating unsaturated compounds, in which particles of a first hydrogenation catalyst are suspended in a liquid phase in which an unsaturated compound is dissolved, the liquid phase, in the presence of a hydrogenous gas at a first partial hydrogen pressure and at a first temperature, is conducted through a packed bubble column reactor in cocurrent counter to the direction of gravity, the effluent from the bubble column reactor is sent to a gas-liquid separation, the liquid phase is sent to a crossfiltration to obtain a retentate and a filtrate, the retentate is recycled into the bubble column reactor and the filtrate, in the presence of a hydrogenous gas at a second partial hydrogen pressure and at a second temperature, is passed over a bed of a second hydrogenation catalyst, wherein the second partial hydrogen pressure is at least 10 bar higher than the first partial hydrogen pressure.

15 Claims, 1 Drawing Sheet

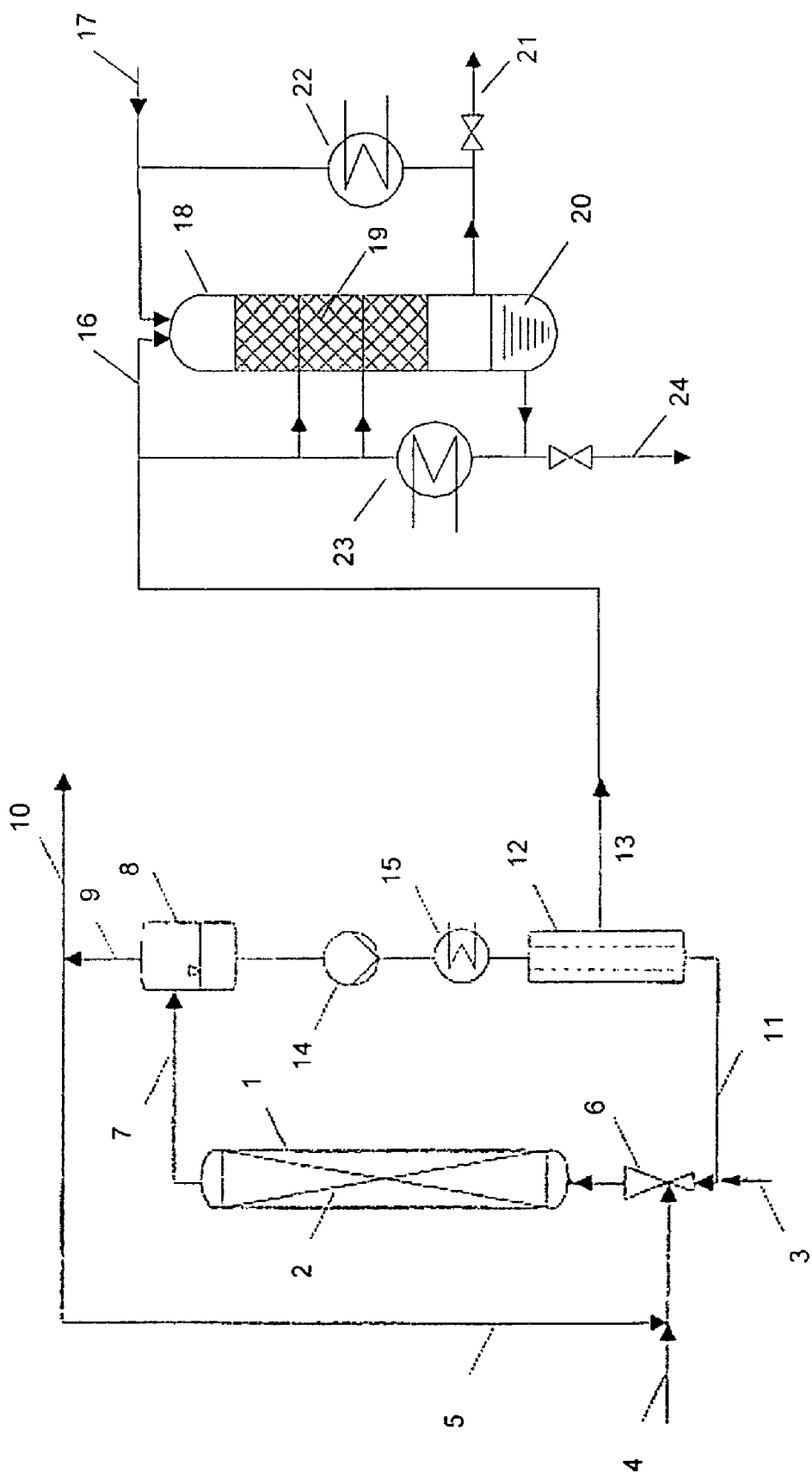

PROCESS FOR CONTINUOUS HYDROGENATION OR HYDROGENATING AMINATION

CROSS REFERENCE TO RELATED APPLICATIONS

This application is a national phase of PCT/EP2006/067470, filed on Oct. 16, 2006, which claims priority to DE 10 2005 049 568.0, filed Oct. 17, 2005, the entire contents of all are hereby incorporated by reference.

The present invention relates to a process for continuous hydrogenation of unsaturated compounds or for continuous hydrogenating amination of carbonyl compounds.

Catalytic hydrogenations over heterogeneous catalysts are in many cases carried out using fixed bed reactors in order to obtain the advantages of a continuous process. For various reactions, fixed bed reactors are, however, unsuitable, since, for a substantially full reaction, they would to have dimensions which are no longer manageable. The amounts of heat which are released in the hydrogenation of unsaturated compounds can cause problems with regard to heat removal in straight pass through a fixed bed reactor. Thus, to reduce the amounts of heat obtained, if appropriate, the conversion has to be restricted and/or the reactor effluent has to be partially recycled, which, though, leads to undesired backmixing. In the case of certain hydrogenations, it is also necessary to prepare and use specially prepared catalysts which, in the case of loss of activity, often even after a short lifetime, have to be exchanged or regenerated. In the fixed bed reactor, a catalyst cannot be changed in the course of operation; the catalyst change is generally associated not only with the shutdown of the hydrogenation plant, but also of the downstream workup stages.

Alternatively, a heterogeneously catalyzed hydrogenation can be carried out in the form of a suspension reaction, in which case the hydrogenation catalyst is suspended in a liquid phase by supply of mechanical energy, for example in a stirred tank; cf., for example, Ullmanns Enzyklopädie der technischen Chemie, 4th ed., Volume 13, 1997, p. 138, Verlag Chemie Weinheim. Continuous stirred tank reactors (CSTR) cannot achieve full conversion of the reactants owing to a high degree of backmixing, since the degree of conversion is a function of the residence time in the reactor and of the reaction rate. In many applications, however, a high degree of conversion of the reactants is desired, especially in the case of preparation of odorants and aromas or pharmaceuticals and crop protection agents or their precursors.

EP-A-0947493 discloses a process for selective liquid phase hydrogenation of α,β-unsaturated carbonyl compounds in a continuous bubble column reactor. However, the disadvantages of this process lie in an incomplete reaction.

The prior art proposes cascade-like arrangements of continuous stirred tank reactors. However, these arrangements have the disadvantage that they require a high financial investment and, in particular, large reactor volume.

DE 196 25 189 C1 discloses a process for catalytic hydrogenation of butynediol to butanediol by a two-stage process. In this process, the butynediol is hydrogenated in a stirred reactor in a first hydrogenation stage, which is followed by a hydrogenation in a fixed bed reactor. This process is intended to reduce the by-product formation of high-boiling components. It is not evident from this publication whether the catalyst is removed continuously.

EP-A 1 676 829, which was published after the priority date of the present application, discloses the manufacture of alicyclic carboxylic acids or their derivatives by selective hydrogenation of the corresponding aromatic carboxylic acid (derivatives) in at least two series-connected reactors, wherein at least one reactor is operated in a loop operating mode.

It is an object of the present invention to provide a process for hydrogenating unsaturated compounds, which combines the advantages of a high space-time yield and of a high conversion with improved process flexibility and low capital cost.

The object is achieved by a process for continuously hydrogenating unsaturated compounds, in which
a) particles of a first hydrogenation catalyst are suspended in a liquid phase in which an unsaturated compound is dissolved,
b) the liquid phase, in the presence of a hydrogenous gas at a first partial hydrogen pressure and at a first temperature, is conducted through a packed bubble column reactor in cocurrent counter to the direction of gravity,
c) the effluent from the bubble column reactor is sent to a gas-liquid separation,
d) the liquid phase from step c) is sent to a crossflow filtration to obtain a retentate and a filtrate,
e) the retentate is recycled into step b),
f) the filtrate, in the presence of a hydrogenous gas at a second partial hydrogen pressure and at a second temperature, is passed over a bed of a second hydrogenation catalyst.

The second partial hydrogen pressure is preferably at least 10 bar higher than the first partial hydrogen pressure.

The ratio of the volume flow rate of the filtrate to the volume flow rate of the retentate is preferably from 1:2000 to 1:10, in particular from 1:500 to 1:10. The degree of conversion in step b) is generally from 80 to 99.8%, preferably from 90 to 99.6%, based on the unsaturated compound fed. The degree of conversion in step f) is generally at least 90%, based on the unsaturated compound present in the filtrate, in particular from 95 to 100%.

Especially in the selective hydrogenation of fragrance and aroma precursors, the hydrogenation process according to the invention has been found to be particularly advantageous. The process according to the invention enables an extremely high conversion (deep hydrogenation), which is of significance precisely in the fragrance and aroma sector, since even the smallest contaminations here, for example from unconverted unsaturated precursors, can considerably distort the odor or taste impression. Deep hydrogenation is suitable in many cases for eliminating troublesome discolorations. The coloring constituents are usually (poly)unsaturated compounds which are converted to colorless compounds by hydrogenation. The hydrogenation process according to the invention can also be used particularly advantageously in the crop protection and pharmaceutical sector, since particularly high requirements are made there with regard to full conversions and product purity thus achievable in view of the introduction of substances into the environment or into the human or animal body.

In the context of the present invention, unsaturated compounds are compounds having multiple bonds to which hydrogen can be added. They are preferably compounds having at least one ethylenically unsaturated C=C double bond and/or C≡C triple bond. A plurality of ethylenically unsaturated C=C double bonds may be present in isolated, cumulated and/or conjugated form.

Also included in the unsaturated compounds are those which comprise at least one carbon-heteroatom double bond, especially carbon-oxygen, carbon-nitrogen, carbon-sulfur, carbon-phosphorus, carbon-silicon double bonds, or carbon-nitrogen or carbon-phosphorus triple bonds. It is also possible for double or triple bond systems between heteroatoms to be hydrogenated with the process according to the invention. Especially included in the unsaturated compounds are organic molecules which have ethylenic double bonds, amide, carboxyl, nitrile, imine, nitro, keto and/or aldehyde groups.

A preferred embodiment relates to the selective hydrogenation of the C=C double bond (with retention of the C=O double bond) of α,β-unsaturated carbonyl compounds. For this purpose, the first and the second hydrogenation catalyst are selected such that they are capable of preferentially hydrogenating carbon-carbon double bonds over carbon-oxygen double bonds.

α,β-Unsaturated carbonyl compounds are especially those of the formula (I) below

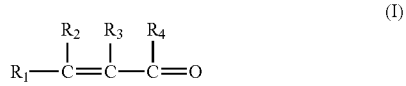

(I)

in which $R_1$ is hydrogen or an organic radical, preferably alkyl (e.g. $C_{1-20}$-alkyl), alkenyl (e.g. $C_{2-20}$-alkenyl), aryl (e.g. phenyl) or aralkyl (e.g. phenyl-$C_{1-6}$-alkyl), and $R_2$, $R_3$ and $R_4$ are each independently hydrogen or $C_{1-4}$-alkyl. The aryl radicals may have up to 1, 2, 3 or 4 substituents such as $C_{1-9}$-alkyl or $C_{1-9}$-alkoxy.

Particularly preferred feedstocks are cinnamaldehyde and cinnamaldehyde derivatives of the following formula (II)

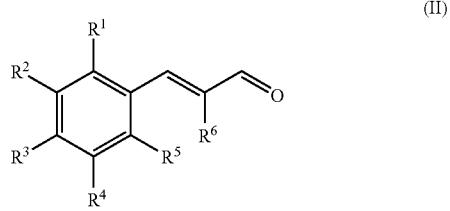

(II)

in which $R^1$, $R^2$, $R^3$, $R^4$ and $R^5$ are each independently hydrogen, $C_{1-9}$-alkyl or $C_{1-9}$-alkoxy, and $R^6$ is hydrogen or methyl.

A preferred cinnamaldehyde derivative is dehydrolysmeral (2-methyl-3-(p-tert-butyl-phenyl)propenal).

Preferred feedstocks are also terpene aldehydes such as citral; and ketones with terpenoid skeleton such as pseudoionone (6,10-dimethylundeca-3,5,9-trien-2-one).

Preferred unsaturated compounds are also enamines which are preferably formed in situ from a carbonyl compound and a primary or secondary amine. In other words, the process according to the invention serves for the hydrogenating amination of carbonyl compounds.

Suitable carbonyl compounds which can be subjected to the hydrogenating amination are, for example, acetaldehyde, propionaldehyde, n-butyraldehyde, isobutyraldehyde, n-pentanal, n-hexanal, 2-ethylhexanal, 2-methylpentanal, 3-methylpentanal, 4-methyl-pentanal, glyoxal, benzaldehyde, p-methoxybenzaldehyde, p-methylbenzaldehyde, phenylacetaldehyde, (p-methoxyphenyl)acetaldehyde, (3,4-dimethoxy-phenyl)acetaldehyde, furfural, 4-formyltetrahydropyran, 3-formyltetrahydrofuran, 5-formylvaleronitrile, hydroformylated polyisobutene (polyisobutene aldehyde, PIBA), hydroformylated oligomers obtained by metathesis of 1-pentene and cyclopentene, acetone, 2-butanone, 3-methylbutan-2-one, 4-methylpentan-2-one, diethyl ketone, tetralone, acetophenone, p-methylacetophenone, p-methoxyacetophenone, m-methoxyacetophenone, 1-acetylnaphthalene, 2-acetylnaphthalenen, 1-phenyl-3-butanone, benzophenone, cyclobutanone, cyclopentanone, cyclopentenone, cyclohexanone, cyclohexenone, 2,6-dimethylcyclohexanone.

A particularly preferred carbonyl compound is 2-methyl-3-(p-tert-butylphenyl)propanal (lysmeral).

For example, the following primary or secondary amines are used: methylamine, dimethylamine, ethylamine, diethylamine, n-propylamine, di-n-propylamine, iso-propylamine, diisopropylamine, isopropylethylamine, n-butylamine, di-n-butylamine, s-butylamine, di-s-butylamine, isobutylamine, n-pentylamine, s-pentylamine, iso-pentylamine, n-hexylamine, s-hexylamine, isohexylamine, cyclohexylamine, aniline, toluidine, piperidine, morpholine, cis-2,6-dimethylmorpholine and pyrrolidine.

Relative to the carbonyl group to be aminated, the amine is used in at least stoichiometric amounts. In general, from 1.5 to 10 molar equivalents of amine are used per mole of carbonyl group to be converted.

Amines prepared with particular preference by the process according to the invention are, for example, N,N-di($C_{1-4}$-alkyl)cyclohexylamine (from cyclohexanone and di($C_{1-4}$-alkyl)amine), n-propylamines (such as dimethylpropylamine) (from propionaldehyde and dimethylamine), N,N-dimethyl-N-isopropylamine (from acetone and dimethylamine), N,N-dimethyl-N-butylamines (from butanal, i-butanal or butanone and dimethylamine, N-ethyl-N,N-diisopropylamine (from acetaldehyde and N,N-diisopropylamine), tris(2-ethylhexyl)amine (from 2-ethylhexanal and di(2-ethylhexyl)amine) and tributylamine (from butanal and dibutylamine).

A particularly preferred embodiment of the process according to the invention relates to the reaction of 2-methyl-3-(p-tert-butylphenyl)propanal with cis-2,6-dimethylmorpholine.

A further application of the process according to the invention relates to the selective hydrogenation of the carbonyl group of a compound which has a carbonyl group, especially an aldehyde group, and a C=C double bond not conjugated therewith, for example the hydrogenation of citronellal to citronellol. For this purpose, hydrogenation catalysts are used which are capable of preferentially hydrogenating carbon-oxygen double bonds over carbon-carbon double bonds.

When the unsaturated compounds to be hydrogenated (or the mixture of carbonyl compound and amine in the case of the hydrogenating amination) and/or the hydrogenation product thereof is liquid under the hydrogenation conditions, the liquid phase may be substantially free of external solvents or diluents. "External solvents or diluents" are considered to be all solvents which are different from the unsaturated compound to be hydrogenated or the carbonyl compound and the amine in the case of the hydrogenating amination or the particular hydrogenation product. This has the advantage that the removal of a solvent after the process has been carried out is no longer required to obtain the desired hydrogenated product.

When used, useful diluents are especially alkanes, cycloalkanes, linear or cyclic aliphatic mono-, di-, tri- or polyethers, aliphatic alcohols. Particularly suitable diluents are $C_1$-$C_6$-alkanols, more preferably $C_1$-$C_4$-alkanols, especially methanol.

In the selective hydrogenation of α,β-unsaturated carbonyl compounds, the addition of a catalytic amount of ammonia or of an aliphatic primary, secondary or tertiary amine can improve the selectivity of the hydrogenation. Tertiary amines, for example tri($C_1$-$C_4$-alkyl)amines, especially trimethylamine, are particularly preferred.

As the first hydrogenation catalyst, it is possible to use commercial suspension catalysts. Especially suitable are catalysts which comprise palladium, rhodium, ruthenium, platinum, iron, cobalt, copper, nickel as hydrogenation-active metals.

Frequently, Raney catalysts are used. The most easily available and therefore most used Raney catalyst is Raney nickel.

For the hydrogenating amination or for the preferential hydrogenation of carbon-carbon double bonds over carbon-oxygen double bonds, suitable catalysts are particularly those which comprise at least palladium as the active component. In addition to palladium, the catalyst may also comprise further active components, for example zinc, cadmium, platinum, silver or a rare earth metal, for example cerium. The catalyst may be used in metallic and/or oxidic form. The active components are preferably applied to a support material. Suitable support materials are, for example, $SiO_2$, $TiO_2$, $ZrO_2$, $Al_2O_3$ or carbon such as graphite, carbon blacks or activated carbon. Owing to its ease of suspendability, activated carbon is preferred. The content of palladium is preferably from 0.1 to 10% by weight, in particular from 0.5 to 7% by weight and more preferably from 2 to 6% by weight, based on the total weight of the catalyst.

For the preferential hydrogenation of carbon-oxygen double bonds over carbon-carbon double bonds, suitable catalysts are particularly those which comprise at least ruthenium as the active component. In addition to ruthenium, the catalyst may also comprise further active components, for example iron. The catalyst may be used in metallic and/or oxidic form. The active components are preferably applied to a support material. Suitable support materials are, for example, $SiO_2$, $TiO_2$, $ZrO_2$, $Al_2O_3$, or carbon such as graphite, carbon blacks or activated carbon. Owing to its ease of suspendability, activated carbon is preferred. The content of ruthenium is preferably from 0.1 to 10% by weight, the content of iron preferably from 0.1 to 5% by weight, in particular from 0.5 to 1.5% by weight, based on the total weight of the catalyst.

Preference is given to using suspension hydrogenation catalyst particles having a mean diameter of from 0.0001 to 2 mm, preferably from 0.001 to 1 mm, more preferably from 0.005 to 0.1 mm.

The suspended catalyst material can be introduced into the liquid phase and distributed therein with the aid of customary techniques.

The hydrogenous gas used, both in the bubble column reactor and in the fixed bed reactor, is generally hydrogen gas having a purity of, for example, at least 99.5% by volume. The amount of hydrogen to be used in both process stages is at least equimolar to the number of double bond equivalents to be hydrogenated in the unsaturated compound in the liquid phase. However, it is customary to work with an excess of from 1 to 20%.

According to the invention, the liquid phase with the suspended first hydrogenation catalyst, in the presence of the hydrogenous gas, is conducted through a packed bubble column reactor in cocurrent counter to the direction of gravity.

The packed bubble column reactor consists substantially of a thin, vertical cylindrical reactor into which a sparging apparatus has been installed in the lower section. The gas distributors used are, for example, porous plates, perforated trays, perforated tubes, nozzles or nozzle trays. The gas phase is fed continuously. In addition, the packed bubble column used in accordance with the invention has packing elements.

The packing brings about a higher relative speed of the liquid phase compared to the catalyst particles because the transport of the catalyst particles is inhibited by the packing in the reactor, i.e. the particles are held back more strongly compared to the surrounding liquid. In conjunction with the higher volume-based surface area of the suspended particles, the space-time yield is increased.

The packing inhibiting the transport of the catalyst particles typically comprises internals in the reactor which are arranged such that the reaction mixture, in passing through the reactor, is forced through the packing, i.e. the internals generally fill the entire free cross section of the reactor. The internals preferably but not necessarily extend over the entire dimension of the reactor in flow direction of the liquid phase.

The packing inhibiting the transport of the catalyst particles preferably has orifices or channels whose hydraulic diameter is from 2 to 2000 times, in particular from 5 to 500 times, more preferably from 5 to 100 times the mean diameter of the catalyst particles.

The hydraulic diameter is a parameter familiar to those skilled in the art for describing the equivalent diameter of noncircular channel structures. The hydraulic diameter of an orifice is a quotient of 4 times the cross section of the orifice and its circumference. In the case of channels having a cross section in the shape of an equilateral triangle, the hydraulic diameter can be described as $2bh/(b+2s)$ in which b is the base, h is height and s is the sidelength of the triangle.

The orifices or channels of suitable packings advantageously have a hydraulic diameter of from 0.5 to 20 mm, preferably from 1 to 10 mm, more preferably from 1 to 3 mm.

Suitable packing elements are in principle, i.e. by their geometric shape, already known from distillation and extraction technology. For the purposes of the present invention, the packings, however, in principle have a substantially smaller hydraulic diameter, regularly by the factor of from 2 to 10, than comparable internals in the field of distillation and extraction technology.

Suitable packing elements are especially metal fabric packings or wire mesh packings, for example of the Montz A3, Sulzer BX, DX and EX design. Instead of metal fabric packings, it is also possible to use packings of other woven, knitted or felted materials. Also suitable are packings of planar or corrugated metal sheets, preferably without perforation or other larger orifices, for example according to the Montz B1 or Sulzer Mellapak designs. Also advantageous are packings of expanded metal, for example packings of the Montz BSH type.

In the process according to the invention, the hydrogenation in the bubble column reactor and in the fixed bed reactor is operated continuously.

The first hydrogenation stage in the packed bubble column reactor is effected generally at a partial hydrogen pressure of from 1 to 100 bar, preferably from 5 to 25 bar.

The temperatures in the bubble column reactor are typically from 25 to 150° C., preferably from 50 to 100° C.

The superficial velocity with which the liquid phase is conducted through the packed bubble column reactor is preferably at least 100 $m^3/m^2h$, preferably from 100 to 500 $m^3/m^2h$, in particular from 150 to 300 $m^3/m^2h$, that of the gas phase more than 5 $m^3$ (STP)/$m^2h$, in particular from 10 to 200 $m^3$ (STP)/$m^2h$. In order to achieve sufficiently high superficial velocities, the retentate from step d) is recycled.

The process according to the invention envisages a crossflow filtration for the removal of the suspended first hydrogenation catalyst. In the crossflow filtration, the medium to be filtered is moved tangentially to the surface of a membrane which allows liquid to pass through but retains the suspended catalyst. The volume stream of the filtrate (permeate) runs at right angles to the flow direction of the medium. The driving force of the process is the transmembrane pressure. In the crossflow filtration, the flow parallel to the filter surface prevents the buildup of a filtercake.

The filter membranes used for the process according to the invention have, depending on the particle size of the catalyst used, preferably pore diameters in the range from 0.5 nm to 20 µm, in particular in the range from 1 nm to 10 µm and most preferably from 2 nm to 1 µm.

The separating layers of the filter membranes may consist of organic polymers (such as polytetrafluoroethylene, polyvinylidene fluoride, polysulfone, polyether sulfone, polyether ether ketone, polyamide), ceramic (such as $\alpha$-$Al_2O_3$, $ZrO_2$, $TiO_2$, SiC or mixed ceramic materials), metal, carbon or combinations thereof, and have to be stable in the reaction medium at reaction temperature. For mechanical reasons, the separating layers are generally applied to a coarser one- or multilayer porous substructure which consists of the same material or a different material than the separating layer. Examples are metallic separating layers on a substructure of metal; ceramic separating layers on a substructure of metal, ceramic or carbon; polymeric separating layers on a substructure of polymer, metal, ceramic or ceramic on metal; or carbon separating layers on a substructure of carbon, metal or ceramic.

The membranes are typically used in pressure-resistant casings which allow the separation between catalyst-containing retentate and catalyst-free filtrate under the pressure conditions required for the filtration. The membranes may be designed in flat, disk, tubular, multichannel element, capillary or wound geometry, for which the corresponding pressure casings which allow separation between retentate and filtrate are available. Depending on the space requirement, one filter element may comprise a plurality of channels. In addition, a plurality of these elements may be combined in one casing to give a module. In a preferred embodiment, metal membranes are used which are, for example, welded with the casings or designed as disks.

The process is preferably operated in such a way that a very thin top layer of catalyst is formed on the retentate side of the membrane. The catalyst-containing liquid phase is therefore preferably passed at high speed through the modules in order to achieve sufficient shear at the membrane surface. Alternatively, shearing can also be generated by motion of the membrane or by stirrer elements between the membranes (rotation or vibration modules).

Troublesome top layers can be removed by brief flow reversal between retentate and filtrate side. For this purpose, the pressure on the filtrate side is raised above the pressure on the retentate side.

The optimal transmembrane pressure is influenced by factors such as the diameter of the membrane pores, the hydrodynamic conditions which influence the top layer buildup and the mechanical stability of the membrane at the operating temperature. It is usually at least 0.1 bar, in particular from 0.2 to 50 bar, preferably from 0.5 to 25 bar. Higher transmembrane pressures usually lead to higher permeate flows. The achievable permeate flows are dependent greatly upon the membrane type and geometry used, upon the process conditions, upon the composition of the catalyst-containing liquid phase, the catalyst concentration and the type of catalyst. The flow rates are typically between 1 and 2000 kg/m$^2$/h. The achievable catalyst retention is more than 99%.

According to the invention, the filtrate is sent to a further hydrogenation stage over a bed of a second hydrogenation catalyst. The conversion over the second hydrogenation catalyst is effected generally in a fixed bed reactor.

Fixed bed reactors are known per se. In a fixed bed reactor, the hydrogenation catalyst in the form of a bed of random packings is arranged in spatially fixed form in a vertical cylindrical vessel with undivided cross section. The liquid phase and the hydrogenous gas are passed over this catalyst bed, and the liquid phase may be passed through either from above or from below and the gas phase may be conducted in cocurrent or in countercurrent thereto.

In the so-called liquid phase mode, the filtrate is conducted through the bed of the catalyst counter to gravity. In this so-called liquid phase mode, there may be expansion of the bed.

In a preferred embodiment, however, the filtrate is introduced at the top of the fixed bed reactor and it is allowed to trickle over the bed of the second hydrogenation catalyst under the influence of gravity.

Both the liquid phase and the hydrogenous gas phase are preferably fed in continuously, partial recycling being possible for both phases.

Also suitable in principle as the second hydrogenation catalyst are the catalyst materials already listed above for the first hydrogenation catalyst. Especially suitable are thus catalysts which comprise palladium, rhodium, ruthenium, platinum, iron, cobalt, copper, nickel as hydrogenation-active metals.

For the hydrogenating amination or for the preferential hydrogenation of carbon-carbon double bonds over carbon-oxygen double bonds, suitable catalysts are particularly those which comprise at least palladium as the active component. In addition to palladium, the catalyst may also comprise further active components, for example zinc, cadmium, platinum, silver or a rare earth metal, for example cerium. The catalyst may be used in metallic and/or oxidic form. The active components are preferably applied to a support material.

The particles of the second hydrogenation catalyst preferably comprise a support material of sufficient mechanical stability, for example oxides of silicon, aluminum, titanium and/or zirconium. A particularly preferred support material is alumina. Particular preference is given to using a palladium catalyst supported on alumina.

The fixed bed hydrogenation catalysts are typically used in the form of piece material or as pellets in cylindrical, tablet or else spherical form. The pellets commonly have diameters of from 1.5 to 3.5 mm and lengths of up to 20 mm. The dimensions of tablets or piece material are typically between 2 and 8 mm.

The hydrogenation in the fixed bed reactor is effected preferably at a temperature which is at least 10° C. higher than the temperature in the bubble column reactor, in particular at least 40° C. higher. The hydrogenation in the fixed bed reactor is effected preferably at reaction temperatures of from 50 to 250° C., preferably from 60 to 200° C. and in particular from 75 to 160° C.

The partial hydrogen pressure in the fixed bed reactor is generally from 15 to 50 bar, preferably from 20 to 100 bar.

The process according to the invention is illustrated in detail by the FIG. 1 appended and the examples which follow.

FIG. 1 shows a schematic of a plant suitable for carrying out the process according to the invention with a reactor (bubble column) 1 with a packing 2 which inhibits the transport of the catalyst particles. Liquid is introduced into the reactor via the lines 3 and hydrogen gas via the line 4. The cycle gas 5 is mixed by means of the mixing nozzle 6 with fresh gas and the suspension 11 circulated by the pump 14. The reactor effluent is conducted via the line 7 into the separation vessel 8 in which the gas phase is separated out and removed via line 9. A part-stream of this amount of gas is withdrawn via line 10 to restrict the accumulation of gaseous impurities and the remaining amount is conducted into the reactor via the line 5. The suspended catalyst remains in the reactor system by virtue of being retained by means of a crossflow filter 12 and only catalyst-free liquid phase leaving via the line 13 and being withdrawn. By means of the heat exchanger 15, the temperature in the suspension reactor system can be adjusted in a controlled manner.

The product withdrawn via the line 13 is fed to the fixed bed reactor 18 via the line 16. In addition, hydrogen is supplied to the fixed bed reactor via line 17. The liquid phase fed via the line 16 is introduced at the top of the fixed bed reactor 18 and trickles over the fixed bed hydrogenation catalyst particles 19 under the influence of gravity. At the end of the catalyst layer, the liquid and the gaseous phase are separated either at reaction temperature in a hot separator 20 or, after passing through a cooler, in a cold separator. The gas phase is removed via the line 21 and the deep-hydrogenated product can be removed via line 24. By means of the heat exchangers 22 and 23, the temperature in the fixed bed reactor system can be adjusted in a controlled manner.

EXAMPLE 1

Hydrogenating amination of lysmeral (2-methyl-3-(p-tert-butylphenyl)-propanal) with cis-2,6-dimethyl-morpholine to fenpropimorph A plant as shown in FIG. 1 was used, which comprised a bubble column (length 500 mm, diameter 20 mm) equipped with a wire mesh packing of customary design (Kanthal). The wire thickness was 0.1 mm, the fold width 1 mm, the angle of inclination of the fold to the vertical 60°. The volume-based surface area of the packing was 2000 $m^2/m^3$ (based on the geometric surface area of the fabric, i.e. a theoretical surface area in which the fabric is considered as smooth surfaces).

The feed used was a mixture of lysmeral and cis-2,6-dimethylmorpholine in a molar ratio of 1:2.5. The feed rate was 100 g/h.

A palladium-carbon suspension hydrogenation catalyst which comprised 5% palladium on activated carbon was suspended in the feed. The reaction was effected continuously at 80° C. and hydrogen pressure 10 bar. The liquid with the suspended catalyst and the gas were conducted through the reactor at a rate of 200 $m^3/m^2$ h in cocurrent counter to the direction of gravity. The conversion was 99.5%. The space-time yield was 425 $kg_{FPM}/(m^3 h)$.

The cross filtration unit comprised a filter candle ($\alpha$-$Al_2O_3$ and $ZrO_2$ with pore width 100 nm) in a crossflow filter casing (d×h=25 mm×176 mm). The transmembrane pressure was 0.3 bar.

The filtrate was used as a feedstock for the postreactor (100 ml/h). The reactor (diameter d=27.3 mm, bed length=230 mm) was a fixed bed reactor filled with palladium-alumina fixed bed hydrogenation catalyst particles. The reaction was carried out at 140° C. and hydrogen pressure 30 bar in trickle mode. The conversion was 92.9%, which means an overall conversion of 99.96%.

EXAMPLE 2

Hydrogenation of dehydrolysmeral (2-methyl-3-(p-tert-butylphenyl)-propenal) to lysmeral (2-methyl-3-(p-tert-butylphenyl)propanal)

A plant as described in Example 1 was used; the feed used was dehydrolysmeral (30% by weight in methanol). A palladium-carbon suspension hydrogenation catalyst which comprised 5% palladium on activated carbon was suspended in the feed. The reaction was effected continuously at 60° C. and hydrogen pressure 10 bar. The liquid with the suspended catalyst and the gas were conducted through the reactor at a rate of 200 $m^3/m^2$ h in cocurrent counter to the direction of gravity. The conversion was 94%. The space-time yield was 0.3 l/(1 h).

The product from the packed bubble column was used as the feedstock for the postreactor (200 ml/h). The reactor (diameter d=27.3 mm, bed length=400 mm) was a fixed bed reactor filled with particles of a palladium-alumina hydrogenation catalyst. The reaction was carried out at 115° C. and hydrogen pressure 30 bar in trickle mode. The remaining dehydrolysmeral (from about 1.0 to 1.5%) was converted fully (well below 0.1%).

What is claimed is:

1. A process for continuously hydrogenating unsaturated compounds, in which
    a) particles of a first hydrogenation catalyst are suspended in a liquid phase in which an unsaturated compound is dissolved,
    b) the liquid phase, in the presence of a hydrogenous gas at a first partial hydrogen pressure and at a first temperature, is conducted through a packed bubble column reactor in cocurrent counter to the direction of gravity,
    c) the effluent from the bubble column reactor is sent to a gas-liquid separation,
    d) the liquid phase from step c) is sent to a crossfiltration to obtain a retentate and a filtrate,
    e) the retentate is recycled into step b),
    f) the filtrate, in the presence of a hydrogenous gas at a second partial hydrogen pressure and at a second temperature, is passed over a bed of a second hydrogenation catalyst.
    wherein the unsaturated compound is selected from the group consisting of cinnamaldehyde derivatives of the following formula (II)

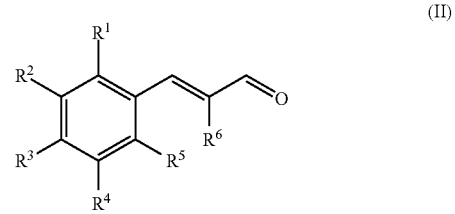

in which $R^1$, $R^2$, $R^3$, $R^4$, and $R^5$ are each independently hydrogen, $C_{1-9}$-alkyl or $C_{1-9}$-alkoxy, and $R^6$ is hydrogen or methyl.

2. The process according to claim 1, wherein the liquid phase is conducted through the packed bubble column reactor in step b) at a superficial velocity of at least 100 $m^3/m^2 h$.

3. The process according to claim 1, wherein, in step f), the filtrate is introduced at the top of a fixed bed reactor and the filtrate trickles over the bed of the second hydrogenation catalyst under the influence of gravity.

4. The process according to claim 1, wherein, in step f), the filtrate is passed through the bed of the second hydrogenation catalyst counter to the direction of gravity.

5. The process according to claim 1, wherein the second partial hydrogen pressure is at least 10 bar higher than the first partial hydrogen pressure.

6. The process according to claim 1, wherein the first partial hydrogen pressure is from 1 to 100 bar.

7. The process according to claim 1, wherein the second partial hydrogen pressure is from 15 to 130 bar.

8. The process according to claim 1, wherein the second temperature is at least 10° C. higher than the first temperature.

9. The process according to claim 1, wherein the first temperature is from 25 to 150° C.

10. The process according to claim 1, wherein the second temperature is from 50 to 250° C.

11. The process according to claim 1, wherein the cinnamaldehyde derivative is 2-methyl-3-(p-tert-butylphenyl)propenal.

12. The process according to claim 11, wherein the liquid phase comprises substantially no external solvent or diluent.

13. The process according to claim 11, wherein the liquid phase comprises an external solvent or diluent.

14. The process according to claim 1, wherein the first hydrogenation catalyst comprises palladium on a carbon support.

15. The process according to claim 1, wherein the second hydrogenation catalyst comprises palladium on an alumina support.

* * * * *